US008597905B2

(12) United States Patent
Fabre et al.

(10) Patent No.: US 8,597,905 B2
(45) Date of Patent: Dec. 3, 2013

(54) METHOD OF DETECTING TUMOR CELLS BY FLUORESCENCE SIGNALS

(75) Inventors: Monique Fabre, Paris (FR); Sophie Ferlicot, Paris (FR); Marie-Pierre Fontaine Aupart, Fresnes (FR); Karine Steenkeste, Villebon sur Yvette (FR); Pascal Eschwege, l'Hay les Roses (FR)

(73) Assignees: Assistance Pulique-Hôpitaux de Paris, Paris (FR); Centre National de la Recherche Scientifique, Paris (FR); Université Paris-Sud 11, Orsay Cedex (FR)

( * ) Notice: Subject to any disclaimer, the term of this patent is extended or adjusted under 35 U.S.C. 154(b) by 0 days.

(21) Appl. No.: 13/381,502

(22) PCT Filed: Jun. 30, 2010

(86) PCT No.: PCT/EP2010/059324
§ 371 (c)(1),
(2), (4) Date: Feb. 24, 2012

(87) PCT Pub. No.: WO2011/000894
PCT Pub. Date: Jan. 6, 2011

(65) Prior Publication Data
US 2012/0264165 A1 Oct. 18, 2012

(30) Foreign Application Priority Data
Jun. 30, 2009 (EP) .................................. 09164258

(51) Int. Cl.
*G01N 21/64* (2006.01)
(52) U.S. Cl.
USPC ...................................................... 435/40.5
(58) Field of Classification Search
USPC ........................................................ 435/40.5
See application file for complete search history.

(56) References Cited

U.S. PATENT DOCUMENTS

2004/0191854 A1* 9/2004 Lapen et al. ................. 435/40.5

FOREIGN PATENT DOCUMENTS

| WO | WO 92/19952 | 11/1992 |
| WO | WO 96/09593 | 3/1996 |
| WO | WO 96/41303 | 12/1996 |

OTHER PUBLICATIONS

Steenkeste et al.; Ex Vivo Fluorescence Imaging of Normal and Malignant Urothelial Cells to Enhance Early Diagnosis, Photochemistry and Photobiology; Sep./Oct. 2007; 83, 5.*
Papanicolaou; A new procedure for staining vaginal smears, Science, 1942, pp. 438-439.*
Trope, et al., "Colony-Forming Ability of Human Ovarian Carcinomas in the Courtenay Soft Agar Assay: Relationship to Clinical Parameters, Histopathology, and DNA Pattern", Gynecologic Oncology, vol. 32, No. 1, (1989), p. 128.
Tang, et al., "Spectroscopic Differences Between Human Cancer and Normal Lung and Breast Tissues", Lasers in Surgery and Medicine, vol. 9, No. 3, (1989), pp. 290-295.
Frable, et al., "Current Practice of Urinary Bladder Cytology", Cancer Research, vol. 37, No. 8, pp. 2800-2805.

(Continued)

*Primary Examiner* — Karen Cochrane Carlson
*Assistant Examiner* — Jennifer M Tichy
(74) *Attorney, Agent, or Firm* — Novak Druce Connolly Bove + Quigg LLP (57) ABSTRACT

The invention relates to a method of detecting dividing cells, or cells having the potential of dividing, in a cytological specimen stained using a Papanicolaou staining process, by the detection of a fluorescence signal coming from the membranes of these cells.

9 Claims, 2 Drawing Sheets

A.

B.

(56) References Cited

OTHER PUBLICATIONS

Hemstreet, et al., "Intravesical CDDP Therapy Compared with Combined CDDP and External Radiation in Noninvasive Bladder Fluorescence Cytology", Urology, vol. 24, No. 1, (1984), pp. 59-63.

Amaral, R.G., et al., "Influence of adequacy of the sample on detection of the precursor lesions of the cervical cancer", Pub Med, vol. 11, pp. 556-560.

Buley, I.D., et al., "Fine-Needle Aspiration Cytology in Tumor Diagnosis: Uses and Limitations", Clinical Oncology, vol. 12, (2000) pp. 166-171.

Cochand-Priollet, B., et al., "Thyroid fine needle aspiration: the morphological features on ThinPrep® slide preparations. Eighty cases with historical control", Cytopathology, vol. 14, (2003), pp. 343-349.

Davies, H.E., et al., "Clinical Impact and Reliability of Pleural Fluid Mesothelin in Undiagnosed Pleural Effusions", American Journal of Respiratory and Critical Care Medicine, vol. 180, (2009), pp. 437-444.

Fan, Y., et al., "Clinical application of the SurePath liquid-base Pap test in cytological screening of bronchial brushing for the diagnosis of lung cancer", Cytotechnology, vol. 62 (2010), pp. 53-59.

Ghali, V.S., et al., "Fluoresence of Pneumocystis Carinii in Papanicolaou Smears", Human Pathology, vol. 15, No. 10 (1984), pp. 907-909.

Hettlich, C., et al., "Aspergillus in the Papanicolaou stain: morphology, fluorescence and diagnostic feasibility", Cytopathology, vol. 9, (1998), pp. 381-388.

Abstract of Küpper, T., et al., "Detection of Charcot-Leyden crystals by fluorescence microscopy of Papanicolaou-stained smears of sputum, bronchoalveolar lavage fluid, and bronchial secretions", Cytopathology, vol. 5, No. 5 (1994), pp. 262-269.

Abstract of Küpper, T., et al., "The cytologic diagnosis of *Mycobacterium kansas* tuberculosis by fluorescence microscopy of Papanicolaou-stained specimens", Cytopathology, vol. 6, No. 5 (1995), pp. 331-338.

Labbé, S., et al., "False negative rate in quality assessment of Pap smears Rescreening from 522 histologically proven lesions", Ann. Pathol., vol. 19, No. 5 (1999), pp. 457-462.

American Journal of Surgery, "The Uniform Approach to Breast Fine-Needle Aspiration Biopsy", vol. 174 (1997), pp. 371-385.

Quddus, M.R., et al., "Does the ThinPrep Imaging System increase the detection of high-risk HPV-positive ASC-US and AGUS? The Women and Infants Hospital experience with over 200,00 cervical cytology cases", CytoJournal, vol. 6, (2009) p. 15.

Volmar, K.E., et al., "Pancreatic and Bile Duct Brushing Cytology in 1000 Cases", Cancer Cytopathology, vol. 108, No. 4, (2006), pp. 231-238.

Waugh, M.S., et al., "Use of the ThinPrep® Method in Bile Duct Brushings: Analysis of Morphologic Parameters Associated With Malignancy and Determination of Interobserver Reliability", Diagnostic Cytopathology, vol. 36, No. 9, (2008), pp. 651-656.

\* cited by examiner

METHOD OF DETECTING TUMOR CELLS BY FLUORESCENCE SIGNALS

RELATED APPLICATIONS

This application is a national stage application (under 35 U.S.C. §371) of PCT/EP2010/059324, filed Jun. 30, 2010, which claims priority of European application 09164258.7 filed on Jun. 30, 2009.

The invention relates to a method of detecting dividing cells, or cells having the potential to divide and replicate, such as transformed cells, in a cytological sample stained using a Papanicolaou staining process, by detecting a fluorescence signal at the membranes of these cells. These cells therefore exhibit a fluorescence signature which is different than that of normal and differentiated cells, and which is correlated with their capacity to divide and replicate.

The cytological study of the cells after fixing on slides and staining makes it possible to characterize the cells present in biological samples when observed under microscope, and to make diagnoses regarding the presence of tumor cells.

Cytology has two major fields of application: large-scale cytology referred to as screening (example: cervical-uterine smears) and specialized cytology in selected patients (examples: urine smears, deep organ cytology, etc). The cells are collected by direct spreading of the biological cell product on slides or, more recently, by collecting the cell product "in a liquid medium" with the aim of increasing the sensitivity of the diagnosis and of providing a stock of cells that are useful for enabling additional techniques (immunocytochemistry, molecular biology). Cytology slides are routinely stained using the Papanicolaou staining process.

Cytology is a method that is particularly advantageous in clinical terms. It is indeed inexpensive and informative, since it makes it possible to directly characterize the cells of the organs that are potentially pathological; it is, however, limited by the decreasing number of trained cytotechnicians and cytopathologists and by the lengthy apprenticeship necessary for mastering this diagnostic method. Indeed, the use of cytology requiring considerable human resources is often replaced with histopathological diagnostic methods in paraffin which are more invasive for the patient and more expensive for our health system. New semi-automated techniques to assist with reading cervical-uterine smears have been developed over the past few years in the cervical cancer screening field.

It would therefore be particularly advantageous to have a simple and effective method demonstrating a broad and robust phenotype of transformed cells, by combining fluorescence observation with cytological staining, which is moreover conventional and to a great extent assessed with a bright field by cytotechnicians and cytopathologists. The strength of this invention is that of providing a new diagnostic power without adding the step of a time-consuming and expensive additional labeling. This process may be partially automatable, allowing assistance for the reading so that the human intervention is reduced only to the verification of areas of slides previously identified as possibly exhibiting pathological cells.

Cytology is a sensitive diagnostic method, mainly for the detection of high-grade malignancy cancers, but, on the other hand, it appears to be of a low sensitivity for the diagnosis of low-grade malignancy cancers, corresponding to a group of lesions classified as "modifications of undetermined significance", the percentage of which varies according to the cells analyzed. These uncertain diagnoses involve repeating the cytological examination, and therefore recalling the patients, with the material and psychological difficulties that this requires, and also a risk of lost follow-up and a loss of chance in certain geographical regions owing to a low medical density. In order to overcome these difficulties, it would be useful to propose a novel diagnostic process which is simple, reproducible, standardized and inexpensive and which saves time for the cytopathologist.

If the literature on diagnostic effectiveness of cytology is analyzed, it is thus possible to show the diagnostic limits for low-grade malignancy lesions.

It is recalled that:

Sensitivity:

is the probability that the diagnosis is positive in individuals suffering from the disease sought (detection of true positives): the test is positive if the patient is suffering from the disease. The sensitivity is low when the number of false negatives is high. The sensitivity is calculated by the formula SE=(number of individuals suffering from the disease in whom the sign is present)/(number of individuals suffering from the disease in whom the sign is present+number of individuals suffering from the disease in whom the sign is absent).

Specificity:

is the probability that the diagnosis is negative in the individuals not suffering from the disease sought (non-detection of true negatives): the test is negative if the patient is not suffering from the disease. The specificity is low when the number of false positives is high. The specificity is calculated by the formula SP=(number of individuals not suffering from the disease in whom the sign is absent)/(number of individuals not suffering from the disease in whom the sign is absent+number of individuals not suffering from the disease in whom the sign is present).

Positive Predictive Value:

is the probability of having the disease if the diagnostic test is positive (i.e. that the patient is not a false positive): the patient is suffering from the disease if the test is positive. The positive predictive value is calculated by the formula PPV=(number of individuals suffering from the disease in whom the sign is present)/(number of individuals suffering from the disease in whom the sign is present+number of individuals not suffering from the disease in whom the sign is present).

Negative Predictive Value:

is the probability of not having the disease if the diagnostic test is negative (that the patient is not a false negative): the patient is not suffering from the disease if the test is negative. The negative predictive value is calculated by the formula NPV=(number of individuals not suffering from the disease in whom the sign is absent)/(number of individuals not suffering from the disease in whom the sign is absent+number of individuals suffering from the disease in whom the sign is absent).

The decrease in the rate of slides that appear as false negatives (increase in the negative predictive value), and also the increase in the sensitivity (obtained in particular by the decrease in the number of individuals suffering from the disease in whom the diagnostic sign is absent) are two components which are essential in the development of a cytological test which meets the requirements mentioned above, and which can thus be automatable.

In an ideal world, the cytopathologist should in fact be able to have access (for verification and making the definitive diagnosis) to the slides of all the patients potentially suffering from the disease sought (and these slides should thus not be discarded, i.e. a negative predictive value of 100%), and all the patients suffering from the disease should correspond to the diagnosis (sensitivity of 100%). This means in fact that a non-correspondence to the diagnosis necessarily implies that the patient is not suffering from the disease.

In uterine cervix pathology, atypical malpighian lesions of undetermined significance (ASC-US) or which cannot exclude a high-grade lesion (ASC-H) according to the Bethesda 2001 system, represent respectively from 2.3 to 5.4% and 0.6% of cases (Quddus M R, et al. Cytojournal. 2009 6; 6:15; Amaral R G et al. Rev Bras Ginecol Obstet. 2008; 30(11):556-60). The rate of false negatives is estimated at 6.88% and that of the atypical lesions of undetermined significance is 10.78% in a French series (Labbé S, Petitjean A, Ann Pathol. 1999; 19(5):457-62). If the data from colposcopy and those from smears are compared, the overall sensitivity of detection of CIN (intraepithelial neoplasias) 2 and 3 is estimated at 68% (Campion M J et al. J Exp Clin Cancer Res 1990 (Suppl): FC/107).

In breast pathology, a fine needle aspiration cytology classified as C3 (atypical or of undetermined significance) corresponds to a risk of malignancy of approximately 20% (NIH The uniform approach of breast fine needle aspiration biopsy. NIH consensus development conference. Am J Surg Pathol 1997; 174:371-85).

In respiratory pathology, the sensitivity of bronchial brushing for the diagnosis of cancer varies between 57.8 and 71.6% (Fan Y B, Cytotechnology. 2010; 62:53-9) depending on the technique used. Pleural cytology has a sensitivity of 35%, a specificity of 100% and a negative predictive value of 82% (Davie H E et al. Am J Respir Crit Care Med. 2009; 180(5): 437-44).

In thyroid pathology, the sensitivity of the cytology for the diagnosis of cancer is estimated at between 81 and 96% depending on the technique used (Buley I D et al. Clin Oncol (R Coll Radiol). 2000; 12(3):166-71; Cochand-Priollet B et al. Cytopathology 2003 December; 14(6):343-9).

In bilio-pancreatic pathology, the bile duct brushings have a low sensitivity of 18 to 67% (Waugh M S, et al. Diagn Cytopathol. 2008; 36(9):651-6). In the series by Volmar et al., which groups together 864 patients and which relates to a series of bilio-pancreatic cytological samples, the overall sensitivity is 52.6%, the specificity is 99.4%, the positive predictive value is 98.9% and the negative predictive value is only 67.1% (Volmar K E at al. 2006; 108(4):231-8).

The performance levels of the cytology in urological pathology are the following:

|  | Low grade | High grade | All grades |
| --- | --- | --- | --- |
| Sensitivity | 26.8% | 77.5% | 61.9% |
| Specificity | 93.1% | 93.1% | 93.1% |
| Positive predictive value | 27.7% | 69.1% | 73.5% |
| Negative predictive value | 92.8% | 95.5% | 88.8% |
| Test accuracy | 87.2% | 90.5% | 85.5% |

According to the AFU [French Association of Urology] report: superficial bladder tumors: Gattegno B., Chopin D. Prog Urol 1:867-875, 2001.

Given these various examples of lack of sensitivity for screening low-grade malignancy tumors, the inventors have developed an innovative diagnostic method (Oncocell test) combining Papanicolaou staining of the cytological samples with fluorescence analysis thereof.

This makes it possible to be able to detect the slides containing cells capable of replicating or dividing (thus potentially carrying tumor cells). A supplementary analysis by bright-field imaging makes it possible to make a definitive diagnosis on the nature of the cells observed.

This method makes it possible to detect the cells capable of replication. These cells exhibit a fluorescence localized at their membrane after Papanicolaou staining and excitation in specific wavelength ranges. The cells thus fluorescent therefore include the tumor cells, but also cells which are not representative of a pathological state, such as hematopoietic cells (polymorphonuclear cells, macrophages, leucocytes), cells of the basal layers of the various epithelia (stem cells, progenitor cells), cells capable of renewal (such as epithelial cells), glandular cells (in particular pancreatic cells), or epithelial cells transformed with a virus (such as the BK virus or the papillomavirus).

Papanicolaou staining is a method that is well known in cytology. It was developed back in 1942, in order to detect cervical-uterine cancer, and is carried out routinely in the various cytology laboratories. It can be carried out automatically in apparatuses that exist on the market.

This method comprises the sequential use of three dyes:
Hematoxylin: the product of hematoxylin oxidation, hematein, is a weak anionic dye with a weak affinity for tissues. However, hematein becomes a dye with a strong affinity for nuclei when it is combined with metal elements such as aluminum. Harris's or Mayer's hematoxylin may be used.
Orange G: this product is used to stain cytoplasms yellow, or orange in the case of the presence of keratin.
EA50: this is a mixture of several dyes: light green, eosin Y and Bismarck brown. Light green is used to stain collagen. It can be replaced with fast green, the strength of which decreases more slowly. Eosin Y is used to stain the cytoplasm. Bismarck brown is not always present in EA50, since it reduces the shelf life. It stains acidic mucins.

The samples are rinsed and dehydrated with alcohol after each staining process.

Cells can be stained with hematoxylin in two different ways: by progressive staining, the reaction being stopped once the desired staining is achieved. It is also possible to stain by regressive staining, in which the sample is saturated, and then destained by means of a dilute aqueous or alcoholic solution of hydrochloric acid until the desired staining is obtained.

This method is thus widely documented in the literature, and well known to those skilled in the art.

The inventors have observed that the cells capable of replication, stained by Papanicolaou staining, exhibit a fluorescence which is induced by excitation at a wavelength below 520 nm, and in particular between 420 and 510 nm. This fluorescence is localized at the membrane of these cells and is observed between 520 and 650 nm.

Thus, the invention relates to a method of detecting cells capable of replication in a cytological sample of cells, said sample having been prepared and stained by Papanicolaou staining, characterized in that, under excitation of said sample at a wavelength below 520 nm, a fluorescence emitted by said sample at a wavelength above 520 nm is observed, said cells capable of replication exhibiting an accumulation of fluorescence localized at their membrane envelope.

The implementation of this method thus makes it possible to discard the slides for which no fluorescence is observed (and which are not therefore carrying cells capable of replication, and not therefore carrying tumor cells). It is then possible to specify the nature of the fluorescent cells on the slides. The cytologist can thus verify the nature of the fluorescent cells by conventional transmission, and identify the other signs of possible malignancy (size of the cells, nucleus, staining of internal components (chromatin), condensation or destruction of nuclear DNA, etc), which depend on the origin of the sample and on the pathological condition considered.

The use of the method according to the invention thus enables the cytologist to study only the slides capable of carrying tumor cells. Moreover, said cytologist only has to observe, by conventional transmission, the areas containing fluorescent cells.

The implementation of this method thus makes it possible to reduce the time spent screening the slides, without any risk of loss of quality in the diagnosis of tumor cells, enabling, on the contrary, the earlier detection of these tumor cells.

In the context of the present invention, a "cytological sample of cells" represents a sample of cells which has been deposited on cytological slides according to methods known in the art, and which will be summarized hereinafter.

It should be noted that the observation, under fluorescent light, of slides stained using Papanicolaou staining has already been described in the prior art. Thus, Küpper et al. (Cytopathology, 1995, 6(5), 331-338) reports the diagnosis of tuberculosis caused by *Mycobacterium kansasi* on cytological samples.

Ghali et al. (Hum Pathol. 1984, 5(10), 907-9) report that *Pneumocystis carinii* exhibit fluorescence when samples stained using Papanicolaou staining are subjected to an infrared light.

Fluorescence of microorganisms in samples stained using Papanicolaou staining has also been reported for *Aspergillus* (Hettlich et al, Cytopathology, 1998, 9(6), 381-8).

It is also possible to detect Charcot-Leyden crystals by subjecting samples stained using Papanicolaou staining to a fluorescence (Küpper et al., Cytopathology. 1994, 5(5), 262-9).

The implementation of the process according to the invention contains several steps, between the taking of the samples from the patient, and the final observation of the slides under fluorescence (optionally followed by the characterization of the fluorescent cells by bright-field optical microscopy observation).

Preparation of Cytology Slides

The first step is the fixing of the cells after a sample has been taken from the patient, and then the depositing of said cells on a cytology slide.

The objective of the fixing step is to maintain the cells of the biological sample in a state which is as close as possible to the natural physiological state. In particular, it is desired to preserve as much as possible the integrity of the membrane and of the extracellular matrix. It is also advisable to preserve the morphological details of the cell, and to avoid activation of the extracellular enzymes and of the coagulation proteins.

Chemical fixing is thus preferentially carried out, by immersing the specimen in a liquid containing a fixative.

Many fixatives which have these properties are known in the art. Thus, formaldehyde-based agents which are particularly suitable for implementing the step of fixing the cells of the cytology slide may be noted. These formaldehyde-based fixatives can be buffered in order to have a neutral pH. They may be aqueous or alcohol-based.

Alcohol (methanol)-based agents may also be used.

It is also possible to work on liquid samples in which the cells are preserved in a medium such as CytoLyt® (Hologic Inc, Bedford, Mass., USA), and to resuspend the cells rapidly in a medium such as PreservCyt® (Hologic Inc, Bedford, Mass., USA). The CytoLyt® solution is a methanol-based buffered preservative solution designed to lyze red blood cells, to prevent protein precipitation, to dissolve mucus, and to preserve the morphology of normal cytological samples. It constitutes a transport medium and is used during the preparation of a sample before treatment thereof. Its purpose is not total microbial destruction.

As mentioned above, this step of chemical fixing of the cells makes it possible to maintain the cells of the specimen as much as possible in a state that is as close as possible to the physiological state, and thus optimizes the implementation of the method according to the invention.

It is therefore preferable for this cell-sample fixing step to be carried out as rapidly as possible (and preferably immediately) following the taking of the biological sample. In any event, it is preferable for said sample to have been fixed within 3 hours, preferably within one hour, more preferably 20 minutes or less, most preferably within 5 minutes following the taking of the biological sample.

Once chemically fixed, the cell sample is deposited and spread on the slide. The sample is then "dried" in order to ensure good adhesion on the slide before staining. This drying can be carried out in the air, in an incubator, in alcohol (such as 2-isopropanol or ethanol), or using a fixative spray. In the latter case, it is common for the fixative to contain copolymers (such as polyethylene glycol), which leaves a thin film on the sample. It is thus preferable to rinse the slide in order to remove this protective film and to guarantee optimum staining of the cells. The slide is rinsed with water if the copolymers of the spray are water-soluble, or with alcohol.

This step of depositing/spreading on a slide is preferably carried out rapidly after fixing of the sample.

Thus, it is preferable for said sample to be fixed on the slide within 72 hours following the taking of the biological sample, preferably within 48 hours following the taking of the sample, preferably within 24 hours following the taking of the sample, even more preferably within 12 hours following the taking of the biological sample.

However, some liquid fixatives may make it possible to store the samples for a relatively long period of time, without them degrading.

It is understood that those skilled in the art can easily find in the prior art various protocols for preparing cytology slides for samples of ENT, urinary, gynecological, thyroid, breast or hematological origin, samples originating from serous membranes (peritoneum, pleura, pericardium, meninges), samples of bronchial origin, or the like. However, even though the fixing modes can vary depending on the organ from which the sample was taken, the fixing of the cells in a liquid fixative rapidly after taking the sample makes it possible to promote the performance levels of the method according to the invention, as indicated above. Alternatively, depositing on a slide with chemical fixing on the slide making it possible to maintain the cells of the biological sample in a state which is as close as possible to the natural physiological state can be envisioned.

Staining of the Cytology Slides

After depositing of the biological samples on cytology slides, the latter are stained by means of the Papanicolaou method, using sequentially the three dyes recalled above.

In one preferred embodiment, the cytological samples are stained less than 24 hours (a few minutes to a few hours (6 to 12 hours)) after depositing on a slide. It is preferable to carry out the Papanicolaou staining within 5 days following the fixing on the cytology slide, and preferably within 48 hours following the fixing on the cytology slide.

As seen above, there is a great variety in the application of the various dyes according to Papanicolaou staining protocols.

However, the inventors have demonstrated the fact that the fluorescence observed at the membrane is due to the localization of EA50 at this level. It is therefore preferable not to saturate the slide with this dye.

Thus, in one particular embodiment, the said sample is stained with EA50 for a period of less than or equal to 5 minutes, preferably approximately 4 minutes.

In one preferred embodiment, the sample is rinsed, after staining with EA50, a first time with 95% or 96% alcohol, preferably for a period of between 30 seconds and 1 minute (preferably approximately 30 seconds), and then a second time with 100% alcohol, preferentially for a period of between 30 seconds and 1 minute (preferably approximately 30 seconds). Xylene is then applied, making it possible to finish the staining. Thus, in this embodiment, the steps of rinsing with alcohol after staining with EA50 are limited.

Generally, it is preferable to implement the staining method in such a way that the rinses after each staining step are effective. The aqueous rinses are carried out under a continuous stream. The alcoholic rinses are short, typically 30 seconds.

Observation of the Cytology Slides

As seen above, the inventors have observed that the cells capable of replication present in a cytological sample stained using a Papanicolaou staining process emit a cell fluorescence signal when they are subjected to an excitatory wavelength. This fluorescence signal is induced by an excitation in visible or near-UV light (wavelength below 520 nm), the fluorescence emission being collected above 520 nm.

Preferentially, the excitation wavelength is between 420 and 510 nm, more preferably between 450 and 490 nm.

The inventors have been able to determine that the accumulation of fluorescence observed at the membrane envelope of dividing cells emits at a wavelength centered on 550 nm. Thus, even though it is possible to detect this fluorescence in a broader range (520 to 620 nm), it is preferable to work at this wavelength or detect the fluorescence emitted in the range between 540 and 560 nm.

Implementation of the Method

The implementation of this method thus makes it possible to sort, among a series of cytology slides, those for which no perimembrane fluorescence is observed (and which do not therefore contain tumor cells), and those for which there are cells that emit fluorescence at the cytoplasmic membrane. These cells will require a control of the tumor or non-tumor nature of these cells by means of a bright-field light examination.

The cytopathologist can identify, by conventional transmission, the possible signs of malignancy (size of nuclei, hyperchromatism, size of nucleoli, increase in nucleo-cytoplasmic ratio, etc.), which depend on the origin of the sample and on the pathological condition under consideration.

Given the strong negative predictive value of the method according to the invention, the implementation thereof thus enables the cytopathologist to study only the slides capable of carrying tumor cells.

One of the major advantages of the method according to the invention is that it uses the slides conventionally observed by cytopathologists, but provides additional information (fluorescence), without adding any particular preparation constraint.

The implementation of this method thus makes it possible to reduce the time spent screening the slides, without any risk of loss of quality in the diagnosis, and to establish, on the contrary, an earlier diagnosis of the tumor cells.

Field of Application of the Method

The method according to the invention has in particular been validated on urinary cytology samples, gynecological and endometrial cytology samples (cervical-uterine smears), pancreatic cytology samples and breast cytology samples.

However, this method is also applicable for all cytologies: needle aspirations of superficial organs (thyroid, breast, lymph node), needle aspiration of deep organs (interpleural space, lymph node, bone marrow, lungs, liver, pancreas, bile ducts, digestive wall, adrenal, kidney, any deep abdominal or retroperitoneal mass, salivary glands), collection of cells in physiological fluids (serous fluids: pleural fluid, ascites fluid; urine; bile; joint fluid; cerebrospinal fluid; hematology), collection of cells by brushing (bronchial, urinary and biliary) and collection of cells after injection of physiological saline: respiratory cytology such as bronchoalveolar lavage, anal smears, ENT sphere, prostate cytology (prostate massage and collection of first urine after massage).

The invention also relates to the process for preparing cytological samples as described above and in the examples.

The invention also relates to the process for staining cytological samples by the Papanicolaou method, as described above and in the examples.

Automation of the Method

As seen above, it is advantageous to be able to automate the first reading of the cytology slides, in order for the cytologist to observe only the slides in which a fluorescence has been observed.

This automation of the various steps of the method should thus allow the cytopathologist to save time, and also allow excellent standardization.

It is thus envisioned that the analysis of the slides be carried out after digitization of said slides using a scanner, or image capture via photographic apparatus.

Thus, the slides are analyzed by fluorescence at various magnifications, in order to demonstrate the specific signatures of the cells capable of replication. The scanned and analyzed slides make it possible to provide the pathologist with an annotated and classified virtual slide, with a major amount of time saved and a major gain in sensitivity. This scanner coupled to a camera is regulated in such a way that it can determine the fluorescence emission in the wavelengths specified above, and centered around 550 nm, under an excitation wave of between 420 and 510 nm (preferably between 450 and 490 nm).

It is also possible to capture the images of the same slides under bright light, the cytopathologist then simultaneously observing the image of the slide under fluorescence and under bright light, and being able to establish the diagnosis of malignancy.

Of course, at any time, the cytopathologist can go back to the original slides in order to observe them directly by a bright field and to verify clusters of questionable cells.

Software for image analysis and recognition of areas of interest on the slide allow the cytopathologist to benefit from assistance with reading via a selection of the fields to be studied.

Thus, the invention also relates to a device for reading a cytology slide stained by Papanicolaou staining, characterized in that it contains means for emitting an excitation wavelength onto said slide, and means for reading the fluorescence emitted by said slide.

The means for emitting an excitation wavelength onto the cytology slide comprise a radiation source which emits in a wavelength range of from 420 to 510 nm, preferably from 450 to 490 nm. It may be a laser.

The means for reading the fluorescence emitted by said slide (more specifically by the cells present on the slide) comprise a sensor which makes it possible to measure the radiation emitted by the slide after excitation. This sensor may also determine the area (or areas) of the slide in which the fluorescence emission is performed. This sensor is regulated in such a way that it can determine the fluorescence emission in the wavelengths specified above, and centered around 550 nm.

Preferably, this device also comprises means for capturing images of said slide (or of several areas of said slide).

These capture means may be a photographic apparatus which will be able to capture the image of the slide (or of cells of the slide) emitting a fluorescence after excitation. It is also preferable for the device to make it possible to capture the image of the same area under direct illumination (i.e. without excitation of the samples).

Preferably, these captured images are stored in a memory (present on the apparatus or remotely situated), in such a way that the cytologist can gain access thereto via a computer means. These images can also be printed.

Thus, the cytologist will be able to verify the samples by comparing both the images showing the fluorescent cells and the images showing the structure of the cells, in order to determine the presence of tumor cells and to define a diagnosis.

In one embodiment, the device comprises means associated with the radiation sensor, which make it possible to analyze the slide illuminated in order to determine the areas capable of exhibiting tumor cells, in particular as a function of the fluorescence emitted (intensity, the shape of the fluorescent component), and which must be studied more precisely. This thus makes it possible to identify the cells of interest (exhibiting a peripheral fluorescence) on the slide, to take a photograph thereof, to illuminate them and to photograph them under nonfluorescent light.

Some patent applications (in particular WO 96/041303 or WO 96/009593) describe means that can be used for determining areas of interest on a slide, and also means which make it possible to classify the samples present on the cytology slide as a function in particular of the fluorescence emitted, as described.

Thus, it is known that cells of blood origin have a smaller diameter than tumor cells in a certain number of samples. It is thus possible to specify a level of diameter below which the cells emitting the fluorescence are not considered to be tumor cells and are not taken into account.

In another embodiment, the device also comprises means which make it possible to stain the cytology slides using the Papanicolaou method. This staining can be carried out by immersing the cytology slides in containers, or by using sprays, as described in WO 92/019952. The automation of the staining of slides using the Papanicolaou method does not present any technical difficulties.

The invention also relates to an automated process for detecting cells having the potential to replicate, on a cytological sample of cells, characterized in that it comprises the steps consisting in:
  a) subjecting the slide comprising said sample to a wavelength of between 420 and 510 nm (preferably between 450 and 490 nm);
  b) identifying the possible areas of the slide in which a fluorescence is emitted at around 550 nm;
  c) capturing an image of these areas under fluorescence;
  d) capturing an image of these areas by conventional transmission microscopy, under visible light;
  e) storing the images obtained in c) and d), such that the images are associated with the slide observed.

Steps a) to e) can be repeated with a new slide.

DESCRIPTION OF THE FIGURES

FIG. 1: FIG. 1.A shows the fluorescence observed for healthy urothelial cells. The fluorescence is diffused in the cytoplasm of these cells. FIG. 1.B shows the accumulation of fluorescence on the membrane envelope of cancer cells (urothelial carcinoma).

EXAMPLES OF PREPARATION OF CELL SAMPLES IN NONGYNECOLOGICAL PATHOLOGY

Example 1

Figure 1:
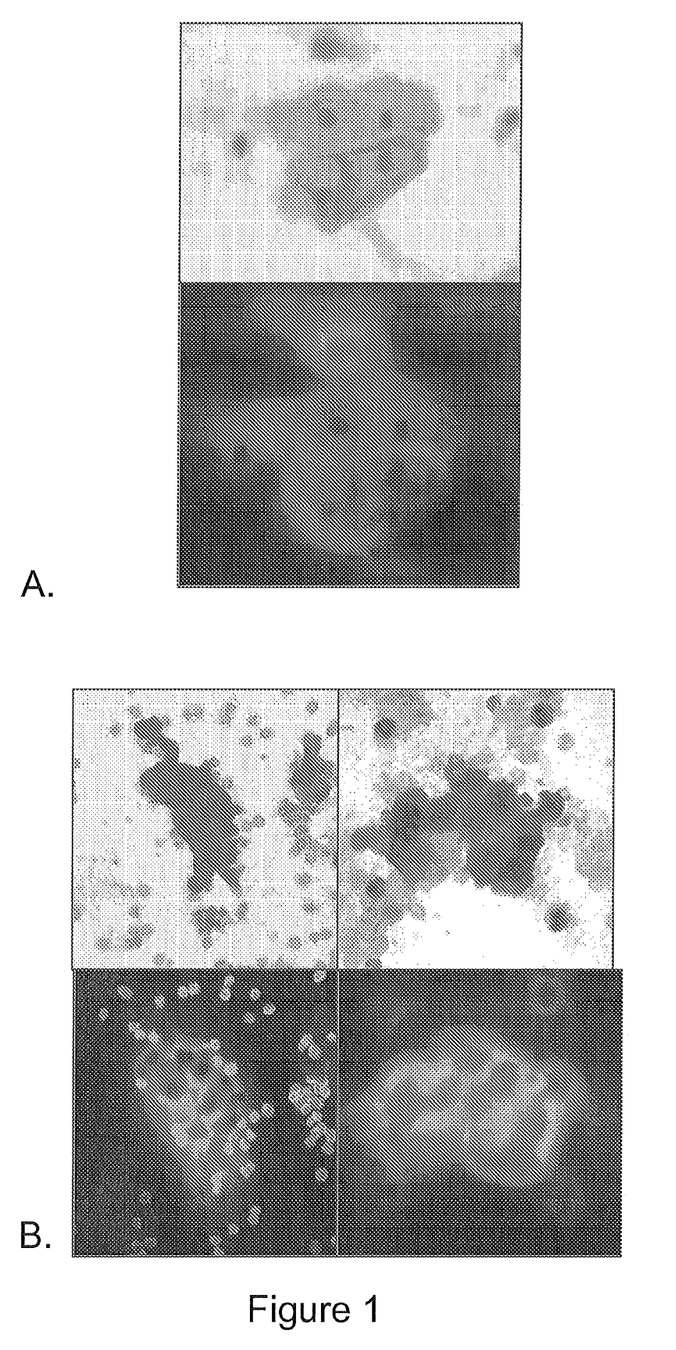
Figure 2:
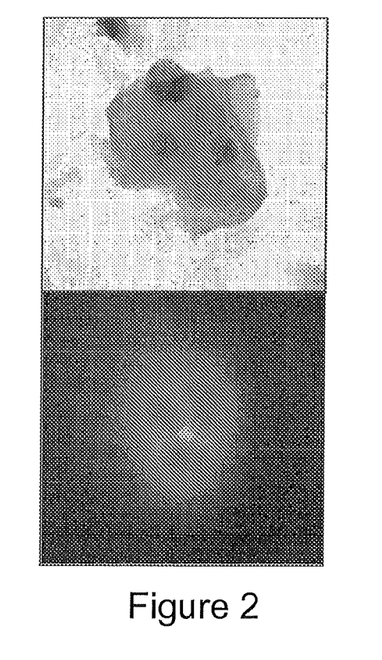
FIG. 2: malpighian cells (healthy) by conventional microscopy and under fluorescence. The fluorescence is diffuse in the cytoplasm of these cells.
Figure 3:
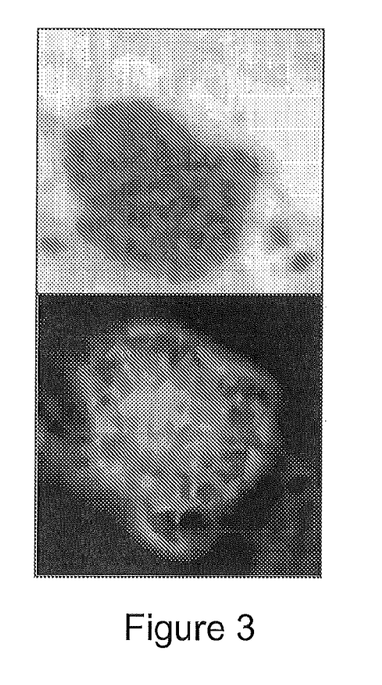
FIG. 3: polymorphonuclear neutrophils observed by conventional microscopy and under fluorescence. These cells, which have the capacity to replicate, exhibit a fluorescence accumulated on the membrane envelope.

Preparation of Slides from Samples of Deep Organs a) For cells received in suspension in CytoLyt®

The sample is concentrated by centrifugation (for example 600G for 10 minutes) and the supernatant is removed.

The sample is then rinsed in a solution of the PreservCyt® type (Hologic Inc). The contact time with the PreservCyt solution is at least 15 min. The PreservCyt® is a buffered solution of methanol which makes it possible to store the cells between 15° C. and 30° C. for 6 weeks.

The cells can then be fixed on a slide using the ThinPrep automated device (Hologic).

The ThinPrep sample vial is placed in a ThinPrep 2000 processor where gentle dispersion disaggregates the blood, the mucus and the debris unsuitable for the diagnosis, and mixes the cells of the sample. The cells are then collected on a filter designed for this purpose and specific for nongynecological specimens. The processor controls the flow rate through the filter in such a way as to avoid them being too abundant or too sparse.

The filter is then turned over onto the slide. A natural attraction and a slightly positive air pressure enable the cells to adhere to the slide. This results in an equal distribution of the cells in a defined circular area.

This slide is thus automatically deposited in a fixing solution containing 95° alcohol for at least 10 minutes before any staining. A thin layer of cells is thus transferred onto a glass slide in a circle 20 mm in diameter.

The staining can then be carried out.

Example 2

Urinary Cytopathology, Urinary Tract Brushings

The samples arrive fixed in formol: 30 ml of fresh urine for 4 ml of 10% formol in a 50 ml conical tube.

The technique is carried out as indicated below:
  the slide identified is introduced into the Shandon Megafunnel® (ThermoFisher);
  2 ml of urine are deposited in the reservoir of the Megafunnel®; the rest of the urine is stored in a refrigerator for at most a week;

the Megafunnel® is placed in the drum of the Thermo Electron® cytocentrifuge at a speed of 4 to 400 to 800 rpm for 10 minutes (program 2);

when the centrifugation is finished, the slide is recovered and it is immediately fixed with the fixing spray or alcohol at 70° C. for a quarter of an hour.

The staining can then be carried out.

Example 3

Bile Cytopathology a) Biliary brushing
The brush arrives in a conical tube containing CytoLyt®.
The brush is vortexed.
The brush is removed and placed in another sterile tube in physiological saline.
The Falcon conical-bottomed tube is centrifuged for 1500 rpm for 10 min in the Jouan centrifuge.
The supernatant is discarded into the liquid waste container.
A little PreservCyt® solution is added to the pellet.
It is stirred well and the entire pellet is transferred into a jar of PreservCyt® of 30 ml.
They are left in contact for a period of at least 15 min, but which may reach several days, at ambient temperature.
A ThinPrep slide is prepared (see example 1).
b) Bile
The fluids are received in the fresh state.
The slides are prepared in the same way as in example 2 (cytofunnel) and can then be stained.

Example 4

Papanicolaou Staining

Running water: 2 min
Hematoxylin solution: 4 min
Running water: 1 min
Solution comprising a mixture of 100% alcohol and of 0.2% HCl: 30 sec
Running water: 10 min
Aqueous ammonia solution at 0.2%: 2 min
70% alcohol: 30 sec
96% alcohol: 30 sec
OG6 solution: 4 min
96% alcohol: 30 sec
96% alcohol: 30 sec
EA50 solution: 4 min
96% alcohol: 30 sec
100% alcohol: 30 sec
Xylene: 30 sec
Xylene: 30 sec
Mounting on a film on slide mounter in xylene solution.

| Components | Reference | Supplier | Packaging |
|---|---|---|---|
| Papanicolaou solution 3b polychrome solution EA50 | HX804463 | Merck KGaA | 2.5 l bottle |
| Papanicolaou solution 2a Orange G in solution (OG6) | HX815072 | Merck KGaA | 2.5 l bottle |

-continued

| Components | Reference | Supplier | Packaging |
|---|---|---|---|
| Hemalun in solution according to Mayer | HX811422 | Merck KGaA | 2.5 l bottle |

Merck KGaA, 64271 Darmstadt, Germany

Example 5

Reading of Samples

The reading is carried out on an epifluorescence optical microscope (excitation wavelengths <520 nm; fluorescence emission wavelengths >520 nm). Such a microscope is part of the equipment of all pathological anatomy and cytology laboratories for routine work.

The interpretation of the cytologies by the pathologist is facilitated: the screening of the tumor cells is carried out as first line under epifluorescence, the characteristics of the dividing cells being an accumulation of fluorescence in the membrane envelope. The quiescent cells (which are not dividing) exhibit diffuse intracytoplasmic fluorescence. It should be noted that the dividing cells also exhibit this cytoplasmic fluorescence, which is, however, barely visible owing to the strength of the cell membrane-bound fluorescence.

When potential cancer cells are detected, confirmation can be carried out by bright-field microscopy.

It should be noted that a decrease in the fluorescent signal (fading) can be observed as the observation period progresses and over time. It is desirable to store the slides in the dark.

This method thus makes it possible to rapidly pinpoint cancer cells in a sample, when they are present in a very small amount.

Example 6

Biological Results

A study was carried out on cytologies performed in patients with a known bladder urothelial carcinoma, or in control patients not suffering from cancer, or on cytologies classified as questionable.

42 patients with urothelial carcinomas were included, including: 22 grade 1 (G1), 5 grade 2 (G2) and 15 grade 3 (G3).

101 patients free of any pathological tumor condition were also analyzed according to the same protocol, as were 26 patients with questionable cytology.

Results: The summary of the results is described in the following tables.

| Urothelial cancers (n = 42) | Cytology − | Cytology + | Questionable cytology |
|---|---|---|---|
| Fluorescence − | 0 | 0 | 0 |
| Fluorescence + | 4 | 24 | 14 |
| Distribution according to | G1:2 G2:2 G3:0 | G1:10 G2:0 G3:14 | G1:10 G2:3 G3:1 |

Cytology sensitivity: 24/42 = 57% (for the G1/G2 = 10/27 (37%); G3 = 14/15 (93%)).
Fluorescence sensitivity: 42/42 (100%).

| Patients without cancer (n = 101) | Cytology − | Cytology + | Questionable cytology |
|---|---|---|---|
| Fluorescence − | 59 | 1 | 36 |
| Fluorescence + | 1 | 2 | 2 |

Sensitivity: cytology 60/101 = 59%
Sensitivity: fluorescence: 96/101 = 95%.

Moreover, 26 suspect cytologies were re-evaluated with fluorescence: 17 positive tests by fluorescence (17 carcinomas discovered), 3 negative tests by fluorescence (3 cases of cystitis), 6 positive tests by fluorescence (5 cases of cystitis and 1 lithiasis).

The method according to the invention therefore indeed makes it possible to improve the cytological study of urinary biological samples and to increase the sensitivity and the negative predictive value.

The invention claimed is:

1. A method of detecting, on a cytological slide, cells that have the ability to replicate, said slide being prepared and stained by Papanicolaou staining, said method comprising
    a) exciting said cells at a wavelength below 520 nm;
    b) measuring fluorescence emitted by said cells at a wavelength above 520 nm;
    wherein cells exhibiting an accumulation of fluorescence localized at their membrane envelope are capable of replication, wherein said cells are from a biological sample that has been fixed on a cytological slide and wherein Papanicolaou staining comprises submitting said slide to the following protocol
    Running water: 2 minutes
    Hematoxylin solution: 4 minutes
    Running water: 1 minute
    Solution comprising a mixture of 100% alcohol and of 0.2% HCl: 30 seconds
    Running water: 10 minutes
    Aqueous ammonia solution at 0.2%: 2 minutes
    70% alcohol: 30 seconds
    96% alcohol: 30 seconds
    OG6 solution: 4 minutes
    96% alcohol: 30 seconds
    96% alcohol: 30 seconds
    EA50 solution: 4 minutes
    96% alcohol: 30 seconds
    100% alcohol: 30 seconds
    Xylene: 30 seconds
    Xylene: 30 seconds.

2. The method as claimed in claim 1, wherein said excitation wavelength is between 450 and 490 nm.

3. The method as claimed in claim 1, wherein said fluorescence emitted at wavelengths of between 540 and 560 nm is observed.

4. The method as claimed in claim 1, wherein said sample was fixed in such a way that the integrity of the membrane and of the extracellular matrix of the cells of the sample was maintained.

5. The method as claimed in claim 1, wherein said sample was fixed with a fixative containing formaldehyde or methanol.

6. The method as claimed in claim 1, wherein said sample was fixed within 3 hours following the taking of the biological sample.

7. The method as claimed in claim 6, wherein said sample was fixed 20 minutes or less after the taking of the biological sample.

8. The method as claimed in claim 1, wherein said sample is chosen from a urinary cytology sample, a cervical-uterine and endometrial cytology sample, a breast cytology sample, a thyroid cytology sample, a salivary gland cytology sample, a respiratory cytology sample, a serous membrane cytology sample, a bilio-pancreatic cytology sample, a hematological cytology sample, a nervous system cytology sample and a prostate cytology sample.

9. A method for staining a cytological slide on which are fixed cells from a biological sample, comprising the step of submitting said slide to:
    Running water: 2 minutes
    Hematoxylin solution: 4 minutes
    Running water: 1 minute
    Solution comprising a mixture of 100% alcohol and of 0.2% HCl: 30 seconds
    Running water: 10 minutes
    Aqueous ammonia solution at 0.2%: 2 minutes
    70% alcohol: 30 seconds
    96% alcohol: 30 seconds
    OG6 solution: 4 minutes
    96% alcohol: 30 seconds
    96% alcohol: 30 seconds
    EA50 solution: 4 minutes
    96% alcohol: 30 seconds
    100% alcohol: 30 seconds
    Xylene: 30 seconds
    Xylene: 30 seconds.

* * * * *